(12) United States Patent
Zhang (10) Patent No.: US 11,364,126 B2
(45) Date of Patent: Jun. 21, 2022

(54) MENISCUS SUBSTITUTE AND KNEE JOINT PROSTHESIS WITH MENISCUS SUBSTITUTE

(71) Applicant: Beijing AK Medical Co., Ltd., Beijing (CN)

(72) Inventor: Weiping Zhang, Beijing (CN)

(73) Assignee: Beijing AK Medical Co., Ltd., Beijing (CN)

( * ) Notice: Subject to any disclaimer, the term of this patent is extended or adjusted under 35 U.S.C. 154(b) by 0 days.

(21) Appl. No.: 16/960,327

(22) PCT Filed: Apr. 4, 2019

(86) PCT No.: PCT/CN2019/081496
§ 371 (c)(1),
(2) Date: Jul. 7, 2020

(87) PCT Pub. No.: WO2020/155377
PCT Pub. Date: Aug. 6, 2020

(65) Prior Publication Data
US 2021/0346164 A1 Nov. 11, 2021

(30) Foreign Application Priority Data
Feb. 1, 2019 (CN) .......................... 201910105032.0

(51) Int. Cl.
*A61F 2/38* (2006.01)
*A61F 2/30* (2006.01)

(52) U.S. Cl.
CPC .......... *A61F 2/3872* (2013.01); *A61F 2/3094* (2013.01); *A61F 2/30749* (2013.01);
(Continued)

(58) Field of Classification Search
CPC .... A61F 2/3872; A61F 2/389; A61F 2/30749; A61F 2002/30011; A61F 2002/30576; A61F 2002/30578; A61F 2002/3092; A61F 2002/3093; A61F 2002/30971; A61F 2/30771; A61F 2002/30784; A61F 2002/30822; A61F 2002/30878; A61F 2002/30968; A61F 2002/30985
See application file for complete search history.

(56) References Cited

U.S. PATENT DOCUMENTS

| 4,919,667 A | 4/1990 | Richmond |
| 6,923,831 B2 | 8/2005 | Fell et al. |

(Continued)

FOREIGN PATENT DOCUMENTS

| CN | 103501732 A | 1/2014 |
| CN | 105813605 A | 7/2016 |

(Continued)

OTHER PUBLICATIONS

The extended European search report of the corresponding EP patent application No. 19912446.2, dated Nov. 19, 2021.

*Primary Examiner* — Javier G Blanco
(74) *Attorney, Agent, or Firm* — Gang Yu (57) ABSTRACT

The disclosure provides a meniscus substitute and a knee joint prosthesis with the meniscus substitute. The meniscus substitute includes: a base body, disposed on a tibial plateau or a tibial plateau prosthesis of a tibia; a polymer joint body, disposed on the base body; and a bone screw, disposed in the tibia in a penetration manner and connected with the base body.

7 Claims, 10 Drawing Sheets

(52) U.S. Cl.
 CPC .............. *A61F 2/30771* (2013.01); *A61F 2002/30784* (2013.01); *A61F 2002/30968* (2013.01); *A61F 2002/30985* (2013.01)

(56) References Cited

U.S. PATENT DOCUMENTS

| | | |
|---|---|---|
| 8,690,955 B2 | 4/2014 | Rolston |
| 2007/0100450 A1 | 5/2007 | Hodorek |
| 2008/0051889 A1 | 2/2008 | Hodorek |
| 2011/0015740 A1 | 1/2011 | Metzger et al. |
| 2018/0193157 A1 | 7/2018 | Fox |
| 2018/0289493 A1 | 10/2018 | Mansmann |

FOREIGN PATENT DOCUMENTS

| | | |
|---|---|---|
| CN | 108186167 A | 6/2018 |
| CN | 108289733 A | 7/2018 |
| JP | 2010517673 A | 5/2010 |
| WO | 2017062397 A1 | 4/2017 |

MENISCUS SUBSTITUTE AND KNEE JOINT PROSTHESIS WITH MENISCUS SUBSTITUTE

CROSS-REFERENCE TO RELATED APPLICATION(S)

The present application claims priority to Chinese Patent Application No. 201910105032.0, filed on Feb. 1, 2019 and entitled "Meniscus Substitute and Knee Joint Prosthesis with Meniscus Substitute", the contents of which are hereby incorporated by reference in its entirety.

TECHNICAL FIELD

The disclosure relates to a field of medical prostheses, and particularly to a meniscus substitute and a knee joint prosthesis with the meniscus substitute.

BACKGROUND

Knee joint is a largest and most complex joint of a human body. A main structure of a knee joint includes a distal femur (femoral condyle), a proximal tibia (tibial plateau) and an articular surface between patellae, and the knee joint may move freely without dislocation mainly because anterior and posterior cruciate ligaments, a medial collateral ligament, a lateral collateral ligament, an articular capsule and tendons attached to the vicinity of the joint provide stability of the joint. In addition, there is a meniscus on each of inner and outer sides of a tibial joint, and the meniscus consists of fibrocartilages, and is located in a joint space of the knee joint. The meniscus is of a semicircular structure, and is relatively thick in periphery and thin and sharp in inner edge; an upper portion is recessed and cooperated to the femoral condyle; and a lower portion is flat and cooperated to the tibial plateau. The meniscus is mainly attached to the tibia but may move within a certain range along with the femur, and a form thereof fills and compensates a fit clearance between a tibia condyle surface and a femoral condyle surface and improves stability of the joint, and may avoid soft tissues around being squeezed into the joint.

At present, meniscus substitutes used by researchers include an autologous tissue graft regenerated meniscus, an allogeneic meniscus graft, a xenogeneic tissue graft substitute and an artificial synthetic material graft substitute. However, present researches show that an effect of replacing a totally removed meniscus with the autologous tissue graft regenerated meniscus is yet not so ideal. A therapeutic effect of the allogeneic meniscus graft is far from proved, and although the meniscus lack of blood supply may be prevented from most problems of the immune system, lack of blood supply may also make a repair capability thereof extremely low and bring a series of problems of source shortage, transportation and storage and the like. Xenogeneic tissue grafting is confronted with more researches and challenges, and there is still a long way to go for clinical application thereof. In the field of researches on artificial synthetic material meniscus substitutes, a lot of work has been done, and absorbable polylactic acid and polyglycolic acid and non-absorbable materials such as polyethylene, polytetrafluoroethylene, polyurethane and a carbon fiber polymer are included. There still exist many problems in terms of simulating a structure, mechanical characteristics and functionality of a human physiological meniscus, including that a meniscus prosthesis may not be stably bonded well with a bone of the tibial plateau, is dislocated beyond expected deformation protrusion under a loaded condition and may not provide effective restrictions for forward, backward and lateral motion ranges of the femoral condyle and the like.

SUMMARY

The disclosure is intended to provide a meniscus substitute and a knee joint prosthesis with the same, to solve the problem of non-ideal therapeutic effect caused by the fact that a meniscus substitute may not provide effective restrictions and may not be stably bonded with a bone in a conventional art.

To this end, according to one aspect of the disclosure, a meniscus substitute is provided, which includes: a base body, disposed on a tibial plateau of a tibia or a tibial plateau prosthesis; a polymer joint body, disposed on the base body; and a bone screw, disposed in the tibia in a penetration manner and connected with the base body.

In some embodiments, the base body includes an integration layer, an isolation layer and a fusion layer, the fusion layer is able to form contact fusion with the polymer joint body, human tissues around the meniscus substitute are able to grow into the integration layer, and the isolation layer is disposed between the fusion layer and the integration layer.

In some embodiments, the isolation layer includes a bottom wall and a sidewall which are disposed at an angle, the bottom wall corresponds to the tibia, the sidewall corresponds to soft tissues around the meniscus substitute, the integration layer includes a bone tissue integration portion and a soft tissue integration portion, the bone tissue integration portion is disposed on the bottom wall, and the soft tissue integration portion is disposed on the sidewall.

In some embodiments, the base body further includes a soft tissue fixing portion, the soft tissue fixing portion is disposed on the sidewall of the isolation layer and extends out of the soft tissue integration portion, the soft tissue fixing portion includes a suture slot and a suture column disposed in the suture slot, and the suture slot and the suture column form a passage that a suture line passes through to bundle and fix the soft tissues on the suture column.

In some embodiments, the base body includes a matrix and an integration layer, a clamping slot is formed in a surface, facing the polymer joint body, of the matrix, a clamping protuberance cooperated to the clamping slot is disposed on the polymer joint body, the integration layer is disposed on a surface, back on to the polymer joint body, of the matrix, a portion, facing one side of a bone bed of the tibia, of the integration layer is a bone tissue integration portion, and a portion, facing the soft tissue around, of the integration layer is a soft tissue integration portion.

In some embodiments, the base body further includes a soft tissue fixing portion, a soft tissue fixing portion is disposed on the matrix, the soft tissue fixing portion includes a suture slot and a suture column disposed in the suture slot, and the suture slot and the suture column form a passage that a suture line passes through to bundle and fix the soft tissues on the suture column.

In some embodiments, the integration layer and/or the fusion layer are/is of a porous structure.

In some embodiments, a pore diameter of the porous structure of the bone tissue integration portion is 150 μm to 1,200 μm, and a pore diameter of the porous structure of the soft tissue integration portion is 400 μm to 2,000 μm.

In some embodiments, the integration layer and/or the fusion layer are/is made by use of a Three-Dimensional (3D) printing technology.

In some embodiments, the integration layer and/or the fusion layer are/is made by use of a metallic particle sintering technology.

In some embodiments, a positioning protruding portion is disposed on the side, facing the bone bed of the tibia, of the base body, a first threaded hole cooperated to the bone screw is formed in the positioning protruding portion, a positioning recess cooperated to the positioning protruding portion is formed in the tibial plateau or the tibial plateau prosthesis, and a second threaded hole for assembling the bone screw is formed in the tibia.

In some embodiments, a first thread and a second thread are disposed at two ends of the bone screw respectively, the first thread is disposed to be cooperated to the first threaded hole of the positioning protruding portion, the second thread is disposed to be cooperated to the second threaded hole in the tibia, and a nominal diameter of the second thread is not smaller than a nominal diameter of the first thread.

In some embodiments, the bone screw is made from a medical metal, and a bone screw with a proper length is able to be adopted for an operation according to a requirement.

In some embodiments, the bone screw is made from an absorbable medical polymer material, for example, poly (lactide-co-glycolide) (PLGA), polylactic acid (PLA) and polycaprolactone (PCL).

According to the other aspect of the disclosure, a knee joint prosthesis is provided, which includes a meniscus substitute, the meniscus substitute being the abovementioned meniscus substitute.

With application of the technical solutions of the disclosure, the bone screw is disposed in a tibia in the penetration manner, and the polymer joint body is disposed on the base body and cooperates with a femur structure. Due to the bone screw and the base body, the meniscus substitute is able to be effectively fixed on the tibia and prevented from being dislocated and deformed beyond an expectation on the tibia. When the femur structure moves relative to the tibia, the surface, facing the femur structure, of the polymer joint body is close to a primary meniscus and is able to be deformed to a certain extent along with rotary compression of the femur structure, so that an attachment area with the femur is ensured, and influence of local overuse damage of the polymer joint body on an overall using effect and service life of the meniscus substitute is avoided.

BRIEF DESCRIPTION OF THE DRAWINGS

The drawings forming a part of the application in the specification are adopted to provide a further understanding to the disclosure. Schematic embodiments of the disclosure and descriptions thereof are adopted to explain the disclosure and not intended to form improper limits to the disclosure. In the drawings.

Herein, the drawings include the following drawing reference signs:

10: base body; 11: integration layer; 111: bone tissue integration portion; 112: soft tissue integration portion; 12: fusion layer; 13: isolation layer; 14: soft tissue fixing portion; 141: suture slot; 142: suture column; 15: matrix; 16: clamping slot; 17: positioning protruding portion; 18: first threaded hole; 20: polymer joint body; 30: bone screw; 41: punching template; 42: first positioning abutting plate; 43: second positioning abutting plate; 44: positioning hole; 45: punch; 46: drilling template; 47: positioning pin; 48: guide hole; 50: suture line; 60: ligament; 70: femur structure; 80: meniscus; 90: tibia; 91: positioning recess; 92: second threaded hole; 93: cortical bone; and 94: cancellous bone.

DETAILED DESCRIPTION OF THE EMBODIMENTS

It is to be noted that the embodiments in the application and characteristics in the embodiments may be combined without conflicts. The disclosure will be described below with reference to the drawings and in combination with the embodiments in detail.

Figure 1:
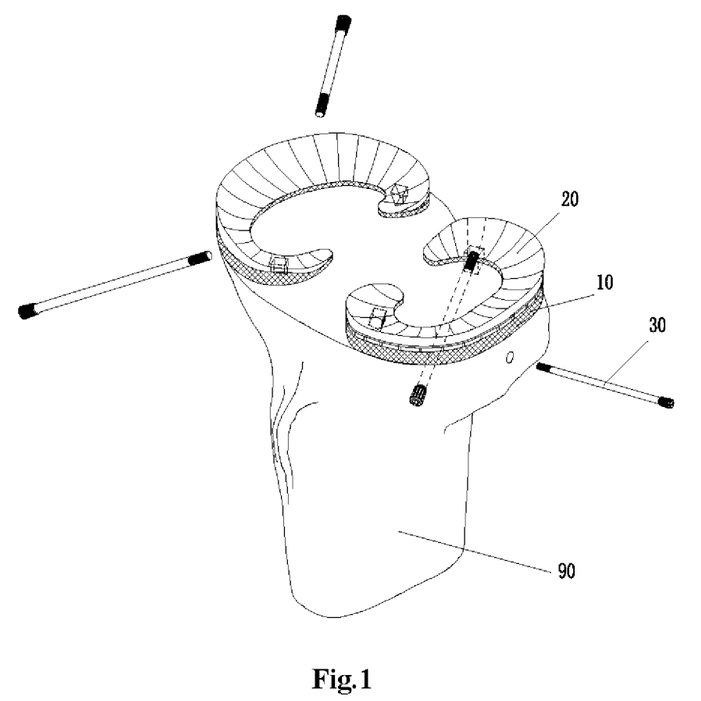
FIG. 1 is a structure diagram of a meniscus substitute according to embodiment 1 on a tibia of the disclosure.
Figure 2:
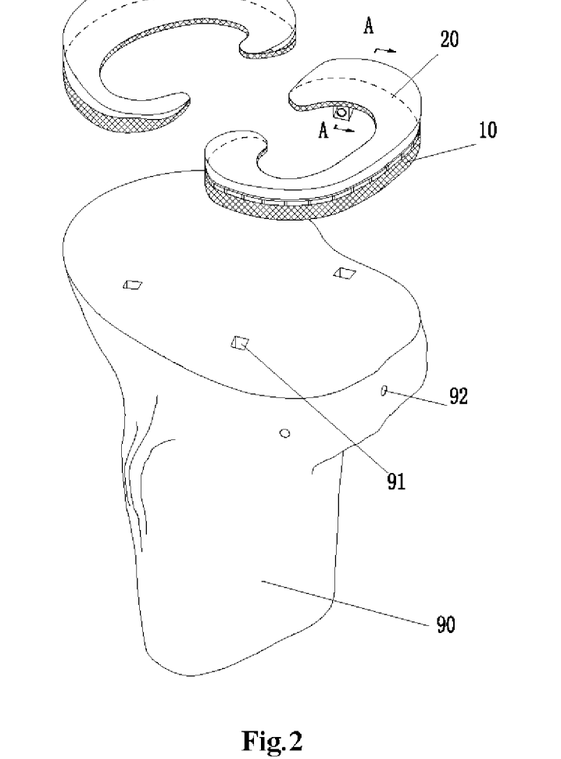
FIG. 2 is a structure diagram when the meniscus substitute in FIG. 1 is separated from the tibia.

As shown in FIG. 1 and FIG. 2, a meniscus substitute according to embodiment 1 includes a base body 10, a polymer joint body 20 and a bone screw 30. Herein, the base body 10 is disposed on a tibial plateau of a tibia or a tibial plateau prosthesis, the polymer joint body 20 is disposed on the base body 10, and the bone screw 30 is disposed in the tibia in a penetration manner and connected with the base body 10 and a bone of the tibia.

With application of the technical solution of the embodiment, the polymer joint body 20 is disposed on the base body 10 and cooperates with a femur structure, and the bone screw 30 is disposed in the tibia in the penetration manner and forms threaded connections with the base body 10 and the tibia respectively. Due to the bone screw 30 and the base body 10, the meniscus substitute is able to be effectively fixed on a tibia 90 and prevented from being dislocated and deformed beyond an expectation on the tibia 90. When the femur structure moves relative to the tibia 90, the surface, facing the femur structure, of the polymer joint body 20 is close to a primary meniscus and is able to be deformed along with rotation of the femur structure, so that an attachment area with the femur is ensured, and influence of local overuse damage of the polymer joint body 20 on an overall using effect and service life of the meniscus substitute is avoided.

Figure 14:
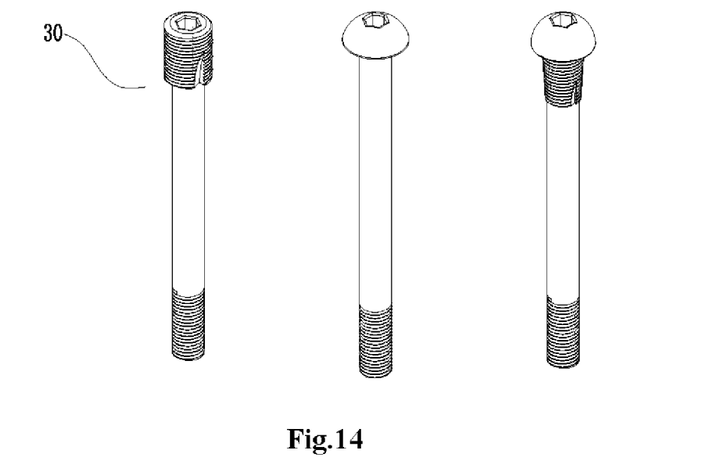
FIG. 14 shows some bone screws applied to the meniscus substitute of the disclosure.

In the meniscus substitute of the embodiment, the bone screw 30 may adopt some screws shown in FIG. 14. As shown in FIG. 1 to FIG. 9, a first thread 31 and a second thread 32 are disposed at two ends of the bone screw respectively, the first thread 31 is disposed to be cooperated to a first threaded hole 18 of a positioning protruding portion 17 of the base body 10, and the second thread 32 is disposed to be cooperated to a second threaded hole 92 on the tibia. Herein, the first thread 31 is preferably a conventional cylindrical thread with a thread pitch of preferably 0.15 mm~3 mm. The second thread 32 may adopt a conventional cylindrical thread or a taper thread, a spiral direction and thread pitch of the thread are the same as a spiral direction and thread pitch of a thread at one end of the positioning protruding portion 17, and the second thread 32 butted with a cortical bone 93 is provided with a self-tapping cutting edge. A screw cap may also be disposed at the end, corresponding to the cortical bone 93, of the bone screw 30 to provide a stronger constraint force in case of insufficient local cortical bone strength of the patient.

Alternatively, the base body 10 is made from a medical metal and/or medical ceramic implantable into a human body, for example, titanium-based, cobalt-based, nickel-based, magnesium-based and tantalum metal alloy materials and austenitic stainless steel. The polymer joint body 20 is made from a medical polymer (for example, but not limited to, polyethylene, polytetrafluoroethylene, polyurethane and carbon fiber polymers) by use of a compression molding and machining method. A joint body locking structure corresponding to the base body 10 is disposed on the polymer joint body 20 to ensure fixed connection between the polymer joint body 20 and the base body 10. The bone screw 30 is made from a medical metal implantable into the human body and/or an absorbable medical polymer material, and the bone screw 30 connects and fixes the base body 10 and the bone of the tibia by a thread.

Figure 3:
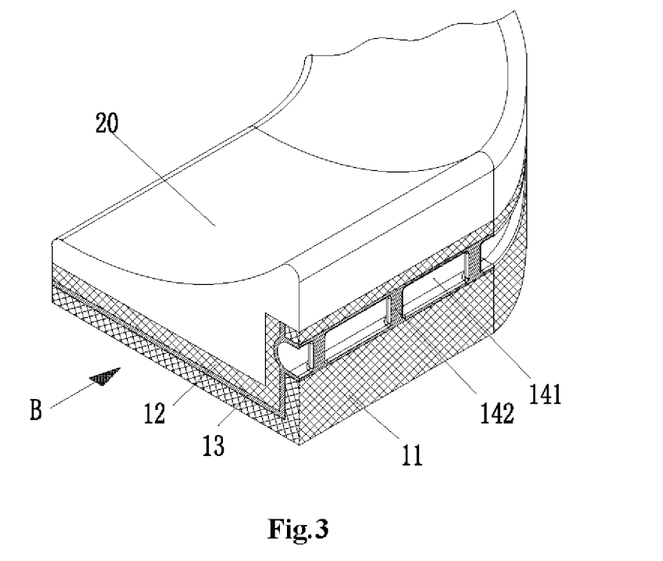
FIG. 3 is a partial enlarged structure diagram of the meniscus substitute in FIG. 2.
Figure 4:
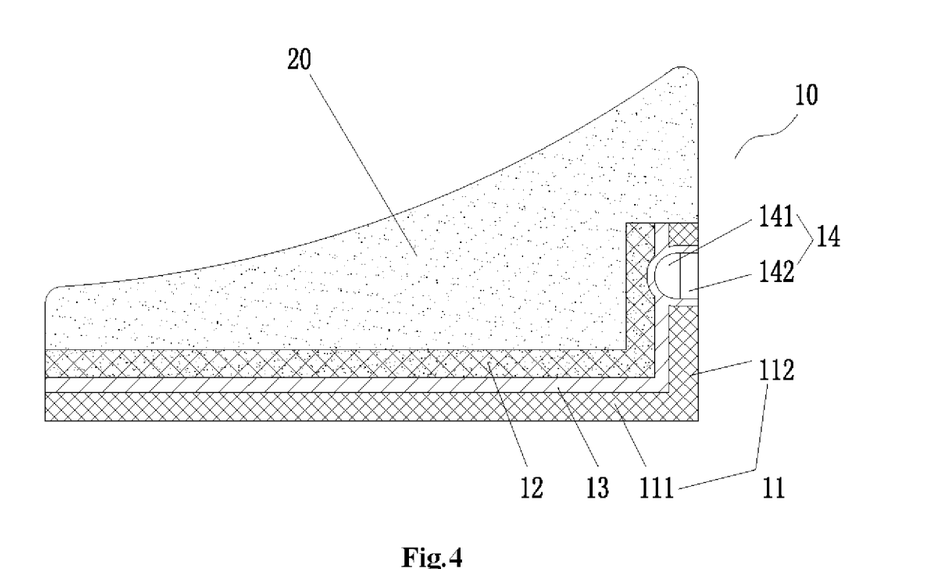
FIG. 4 is a structure diagram of the meniscus substitute in FIG. 3 in a B direction.

As shown in FIG. 3 and FIG. 4, in the embodiment, the base body 10 includes an integration layer 11, an isolation layer 13 and a fusion layer 12. The integration layer 11 and the fusion layer 12 are porous structures made by a 3D printing technology or a metal or ceramic sintering technology. A pore diameter of the fusion layer 12 preferably ranges from 500 µm to 3,000 µm, and such a pore diameter range facilitates adoption of a compression molding method in a making process of the polymer joint body 20 for compression permeation of the polymer material into pores of the porous structures and fusion of the polymer joint body 20 and the base body 10 through a thermoforming or thermosetting molding process to strengthen connection strength of the polymer joint body 20 and the base body 10. For avoiding a relatively strong cutting effect, caused by excessively small sizes, of spacing walls or connecting wires between the pores of the porous layer on the polymer material, thicknesses of the spacing walls or diameters of the connecting wires between the pores of the fusion layer 12 are preferably 0.5 mm~3 mm.

The isolation layer 13 is a physical metal or ceramic layer and disposed between the fusion layer 12 and the integration layer 11, has a thickness of preferably 0.2 mm~2 mm, and is disposed to prevent unexpected permeation and occupancy of the polymer material over pore spaces of the integration layer 11 and fusion layer 12 of the base body 10 in a compression molding process.

Figure 5:
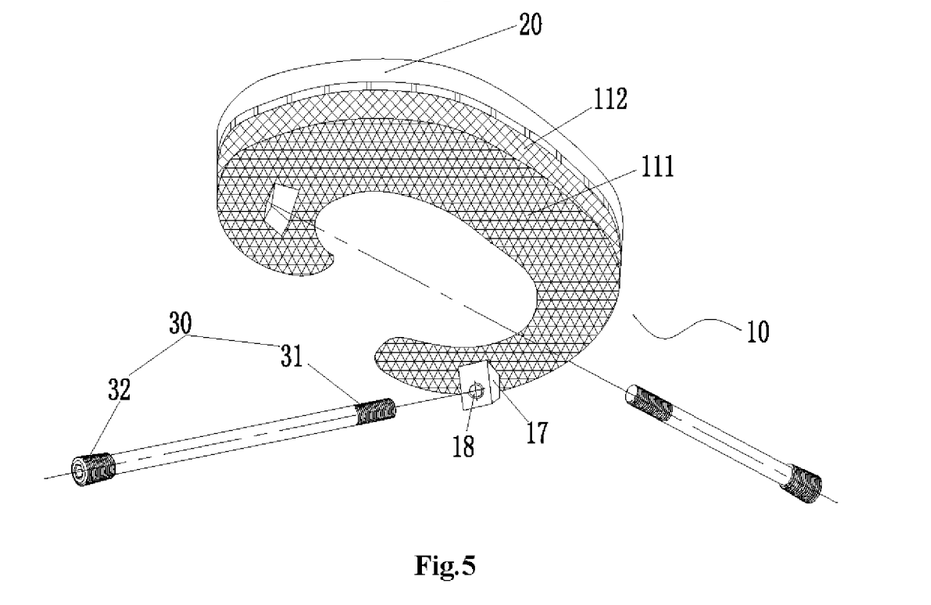
FIG. 5 is a structure diagram of the meniscus substitute in FIG. 2 at another viewing angle.

Similar to the fusion layer 12, tissues around the meniscus substitute, for example, the cortical bone and cancellous bone of the tibia 90 and soft tissues like ligaments, may also grow into the integration layer 11. As shown in FIG. 4 and FIG. 5, the isolation layer 13 includes a bottom wall and a sidewall which are disposed at an angle, the bottom wall corresponds to the tibia 90, and the sidewall corresponds to the soft tissues around the meniscus substitute. Correspondingly, the integration layer 11 includes a bone tissue integration portion 111 and a soft tissue integration portion 112. The bone tissue integration portion 111 is disposed on the bottom wall. When the meniscus substitute is implanted into a knee joint of the patient, the bone tissue integration portion 111 may be attached to a bone surface of the tibia of the patient, and then the bone of the tibia may grow into the pores of the bone tissue integration portion 111. The soft tissue integration portion 112 is disposed on the sidewall, which is also favorable for ingrowth of the soft tissues.

Preferably, in the embodiment, a pore diameter of the porous structure of the bone tissue integration portion 111 is 150 µm to 1,200 µm. and such a pore diameter range is favorable for inducing ingrowth of bone cells to form bone tissue fusion integration. A pore diameter of the porous structure of the soft tissue integration portion 112 is 400 µm to 2,000 µm. and such a pore diameter range is favorable for inducing ingrowth of soft tissue cells to form soft tissue fusion integration.

Of course, it can be understood that, in another embodiment not shown in the figures, the integration layer and the fusion layer may also be machined into the porous structures or other structures favorable for ingrowth of the bone tissues and the soft tissues by other technical means such as plasma spraying, metallic particle sintering, laser drilling and high-energy beam fusion covering.

For further promoting integration between the soft tissues and the soft tissue integration portion 112, as shown in FIG. 3 to FIG. 6, the base body 10 of the embodiment further includes a soft tissue fixing portion 14, and the soft tissue fixing portion 14 is disposed on the sidewall of the isolation layer 13 and extends out of the soft tissue integration portion 112. The soft tissue fixing portion 14 includes a suture slot 141 and a suture column 142 disposed in the suture slot 141, and the suture slot 141 and the suture column 142 form a passage that a suture needle and a suture line pass through to bundle and fix the soft tissues on the suture column 142. The suture column 142 provides a mechanical fulcrum for bundling and fixing for the suture line such that the soft tissues such as the ligaments may be closely attached to the porous structure of the soft tissue integration portion 112 and, in a postoperative healing process, the soft tissues such as the ligaments may grow into the pores of the porous structure.

Figure 6:
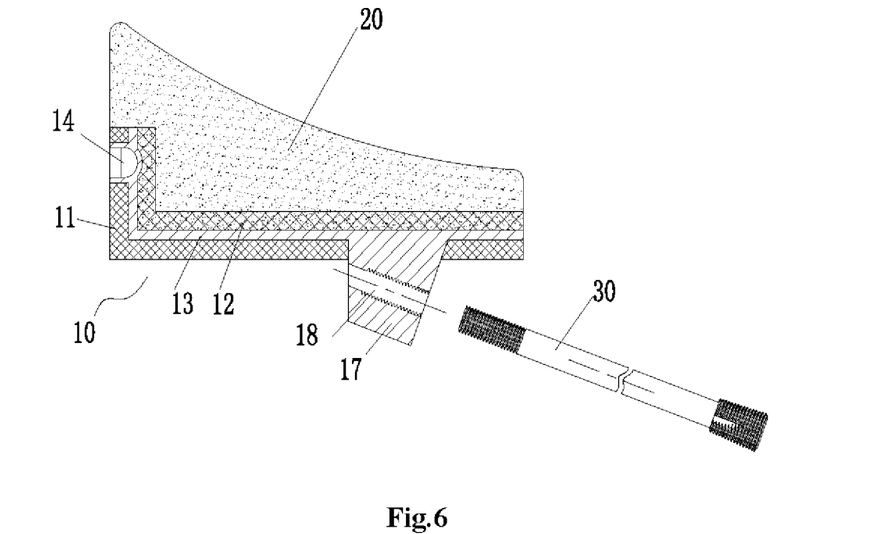
FIG. 6 is a section view of the meniscus substitute in FIG. 3 in an A-A direction.

As shown in FIG. 2, FIG. 5 and FIG. 6, in the embodiment, a positioning protruding portion 17 is disposed on the side, facing the tibia, of the base body 10, a first threaded hole 18 is formed in the positioning protruding portion 17, and the first threaded hole 18 is cooperated to the first thread 31 of the bone screw 30. A positioning recess 91 cooperated to the positioning protruding portion 17 is formed in the tibia 90, and a second threaded hole 92 for assembling the bone screw 30 is formed in the tibia 90. The bone screw 30 is inserted into the tibia 90 through the second threaded hole 92 and cooperates with the first threaded hole 18, and then the second thread 32 at the tail end of the bone screw 30 cooperates with the second threaded hole 92 in the tibia 90. In the embodiment, the tibia is the tibia of the patient. In another embodiment not shown in the figures, the tibia may also be a tibial prosthesis disposed on the tibia of the patient.

Figure 7:
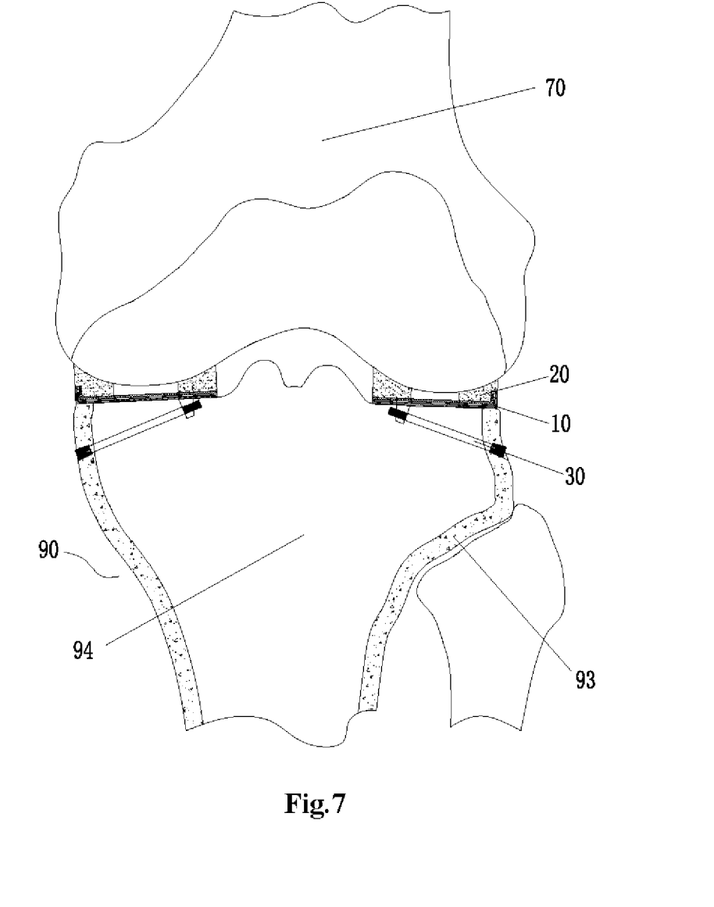
FIG. 7 is a front view of the meniscus substitute in FIG. 1 between a femur and the tibia.
Figure 8:
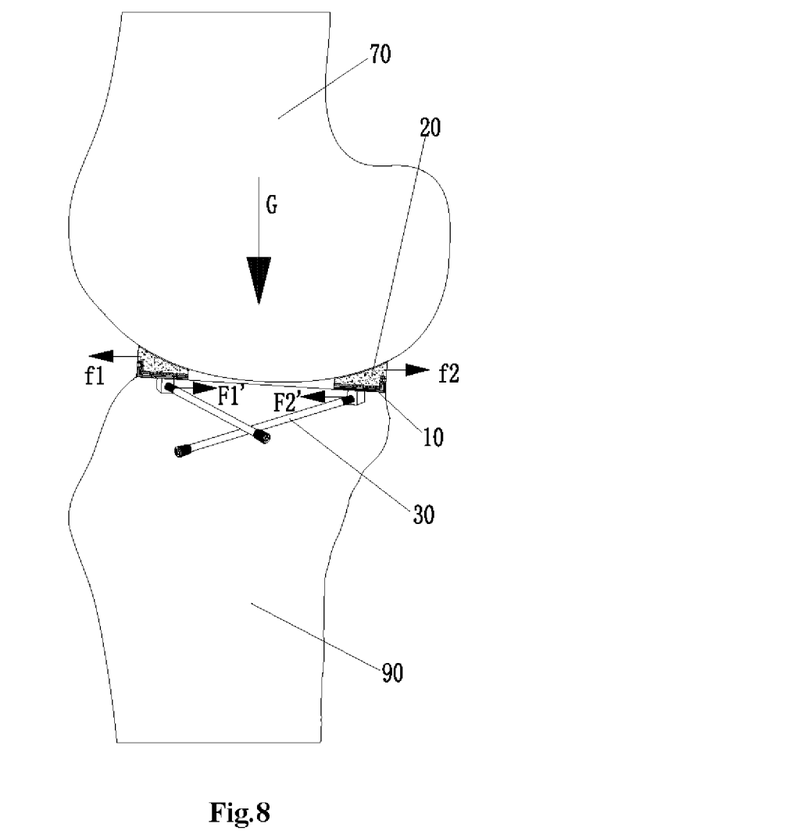
FIG. 8 is a side view of the meniscus substitute in FIG. 7 at another viewing angle.
Figure 9:
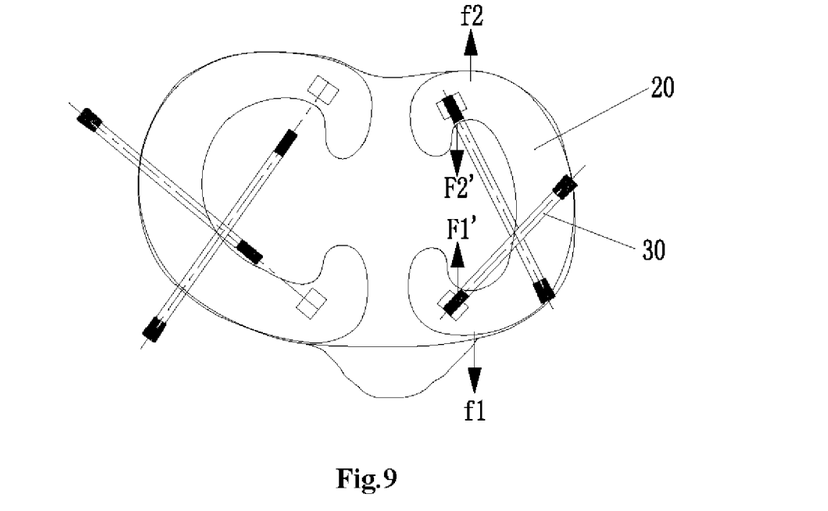
FIG. 9 is a top view of the meniscus substitute in FIG. 7.

The meniscus substitute of the embodiment is wholly of "C"-shaped, and may completely substitute inner and outer menisci of the patient. As shown in FIG. 7 to FIG. 9, two positioning protruding portions 17 are disposed on each meniscus substitute, and the two positioning protruding portions 17 are disposed at an anterior angle and relief angle of the meniscus substitute respectively to make the meniscus substitute closer to a mechanical form of the primary meniscus. The bone screw 30 is obliquely inserted into the cancellous bone 94 of the tibia 90. One end of the bone screw 30 is fixedly connected with the base body 10, while the other end is fixedly connected with the cortical bone 93 of the tibia 90. The polymer joint body 20 is disposed on the base body 10 and contacts and fits with the femur structure 70. Under the action of a load G of the patient, the femur structure 70 and the tibia 90 get close to each other and squeeze the polymer joint body 20 to enable the meniscus substitute to generate a forward bulging force f1 and a forward bulging force f2. In such case, the two positioning protruding portions 17 transmit the bulging forces into the cortical bone 93 of the tibia 90 through the respective bone screws 30 and generate a constraint force F1' and a constraint force F2', and the bulging forces and the constraint forces are counteracted to stabilize the meniscus substitute.

Of course, it can be understood that, in another embodiment, one or more positioning protruding portions may also be disposed on the meniscus substitute according to a size of the meniscus substitute.

Figure 10:
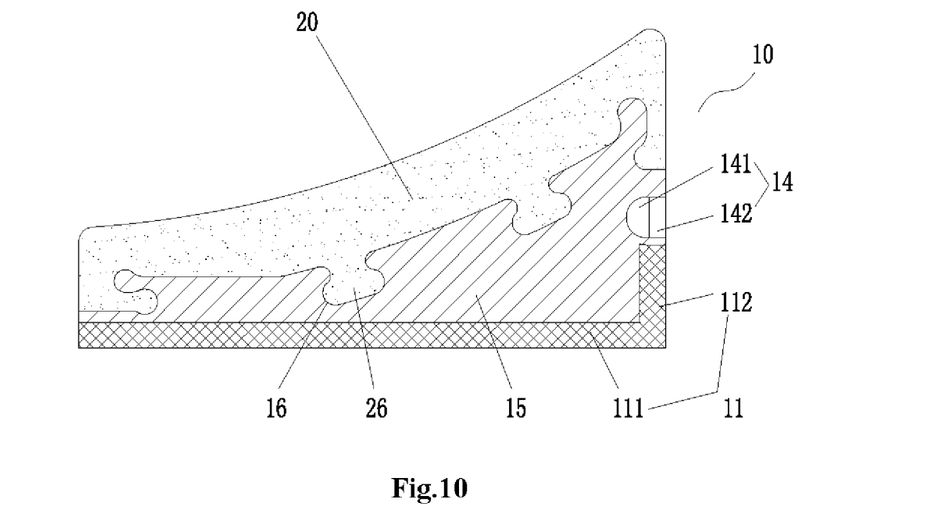
FIG. 10 is a structure diagram of a meniscus substitute according to embodiment 2 of the disclosure.

For the meniscus substitute of embodiment 2, a structural form of the base body 10 and a manner of connection with the polymer joint body 20 are changed on the basis of embodiment 1. As shown in FIG. 10, the base body 10 in embodiment 2 includes a matrix 15 and the integration layer 11. The integration layer 11 is disposed on the side, facing the tibia, of the matrix 15 such that the soft tissues around the meniscus substitute may form contact fusion with the integration layer 11. A clamping slot 16 is formed in the surface, facing the polymer joint body 20, of the matrix 15, and a clamping protuberance 26 cooperated to the clamping slot 16 is disposed on the polymer joint body 20. Clamping fit between the clamping protuberance 26 and the clamping slot 16 implements fixed connection between the base body 10 and the polymer joint body 20. Such a structure provides an opportunity and possibility for selection of different specifications in an operation process and replacement in case of damage to the joint body in a later period.

Correspondingly, in the embodiment, the soft tissue fixing portion 14 is disposed on the matrix 15, structures and functions of the suture slot 141 and suture column 142 of the soft tissue fixing portion 14 are the same as those in embodiment 1, and the suture slot 141 and the suture column 142 form the passage that the suture line passes through to bundle and fix the soft tissues on the suture column 142.

Figure 11:
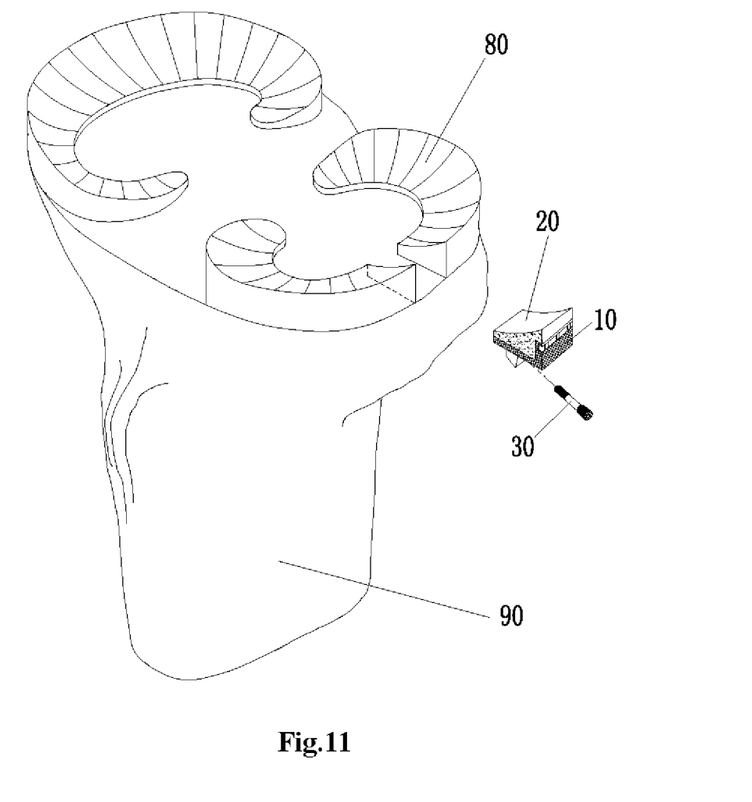
FIG. 11 is a structure diagram of a meniscus substitute according to embodiment 3 of the disclosure.
Figure 12:
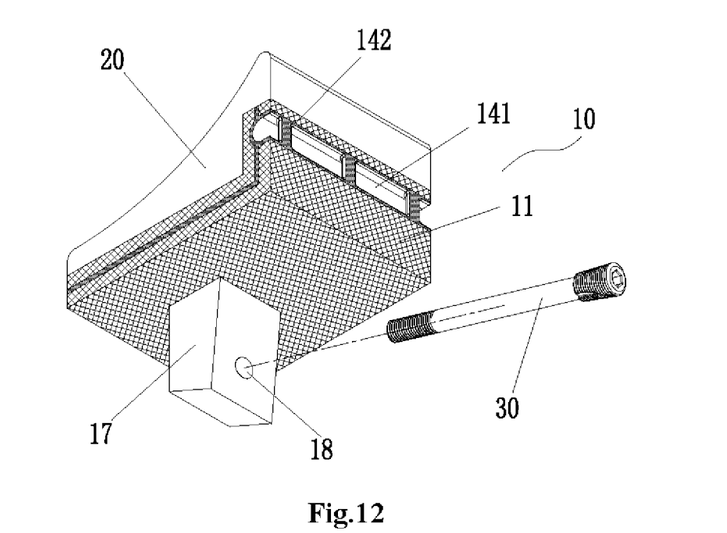
FIG. 12 is a structure diagram of the meniscus substitute in FIG. 11 at another viewing angle.
Figure 13:
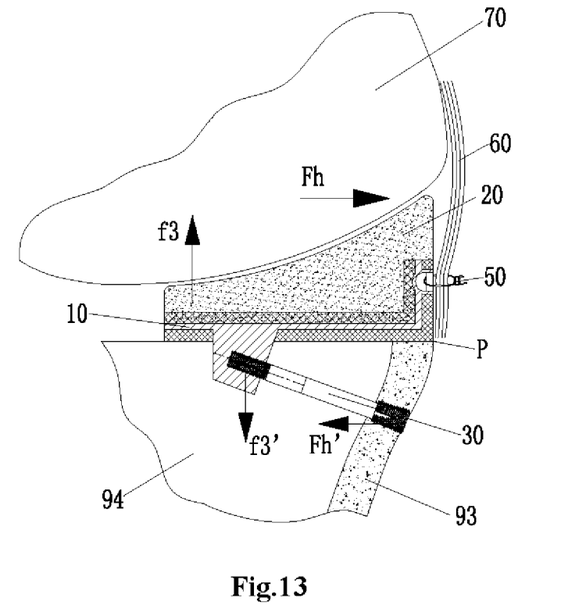
FIG. 13 is a section view of the meniscus substitute in FIG. 12 between a femur and a tibia.

For the meniscus substitute of embodiment 3, a substitution manner is changed on the basis of embodiment 1. As shown in FIG. 11 to FIG. 13, the meniscus substitute of embodiment 3 only substitutes a part of the primary meniscus 80 of the patient, and an overall structure thereof is substantially the same as that of the meniscus substitute of embodiment 1. As shown in FIG. 13, one end of the bone screw 30 is inserted into the cancellous bone 94 and connected with the positioning protruding portion, while the other end is fixed on the cortical bone 93. The ligament 60 is bundled on the suture column 142 through the suture line 50.

When the patient moves after an operation, the femur structure 70 may generate a movement force Fh in a horizontal direction relative to the meniscus substitute, and a straight-up force f3 may be generated on an inner side of the meniscus substitute by taking P as a fulcrum. In such case, the force may be transmitted to the cortical bone 93 through the bone screw 30, and a straight-down counter-force f3' and a horizontal leftward counter-force Fh' are generated to stabilize the meniscus substitute.

Figure 15:
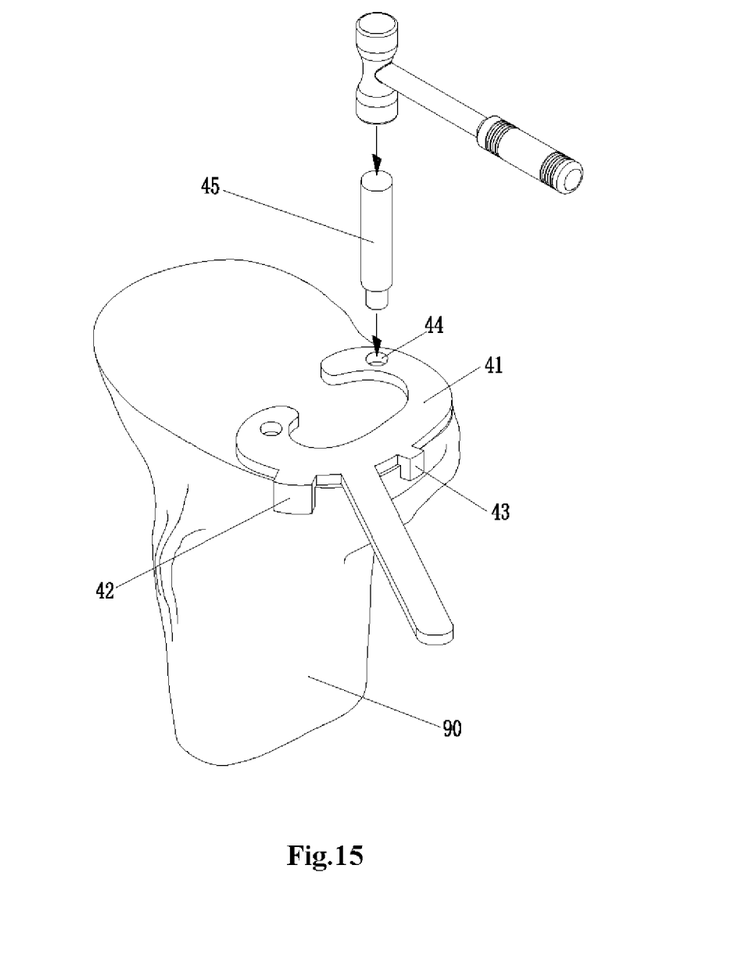
FIG. 15-FIG. 18 are schematic diagrams of a mounting process of the meniscus substitute according to embodiment 1 of the disclosure.
Figure 16:
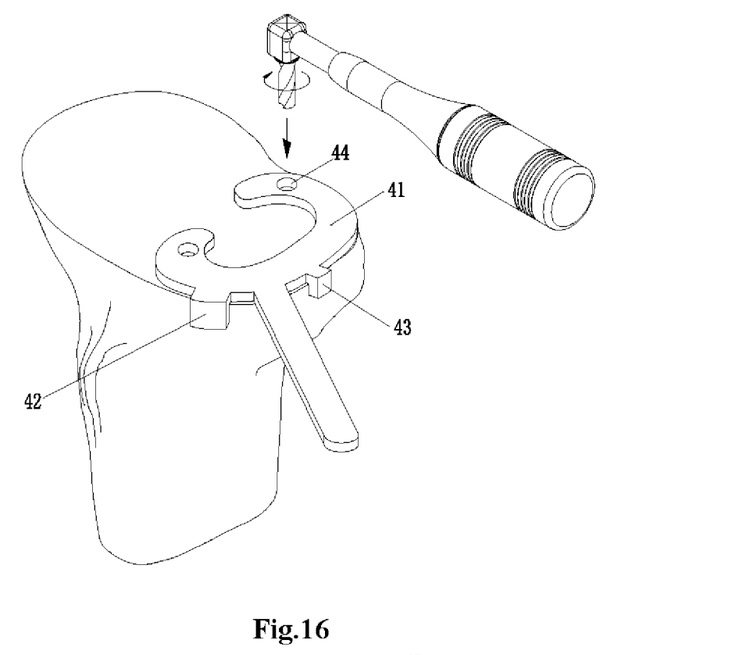
Figure 17:
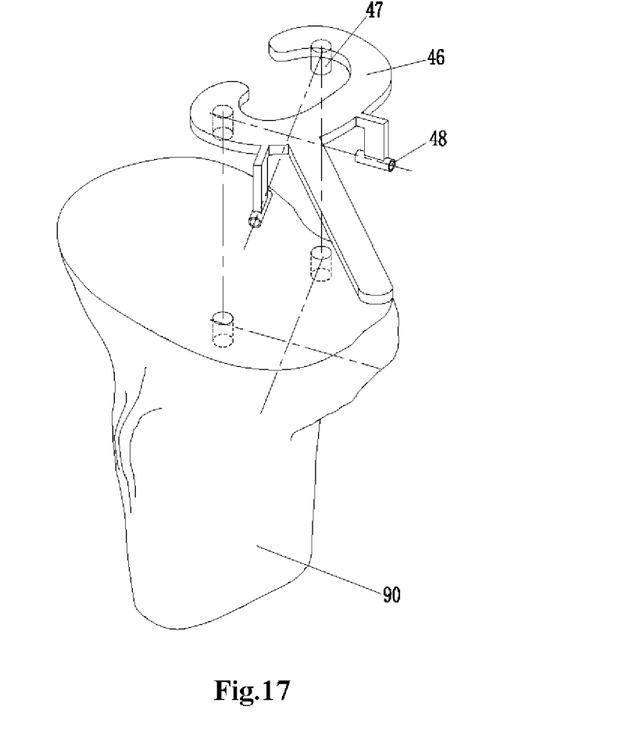
Figure 18:
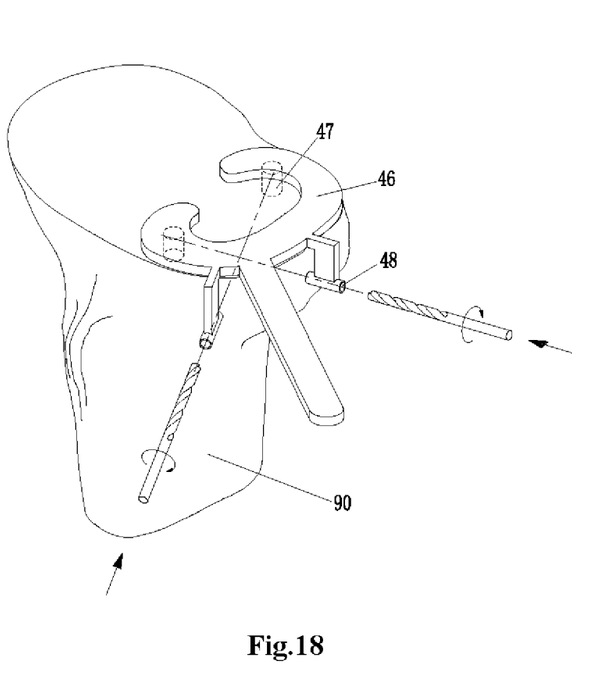

FIG. 15 to FIG. 18 show an operation process of the meniscus substitute according to embodiment 1 of the disclosure. As shown in FIGS. 15 and 16, a punching template 41 is stabilized on the tibia 90 through a first positioning abutting plate 42 and a second positioning abutting plate 43, and punches 45 penetrate through positioning holes 44 in the punching template 41 to determine a position of the positioning protruding portion on the tibia 90 and drill the positioning recess at this position. As shown in FIG. 17 and FIG. 18, a shape of a drilling template 46 is substantially the same as that of the punching template 41, positioning pins 47 extend into the positioning holes 44 to position guide holes 48, and a passage that the bone screw passes through is drilled. Finally, the positioning protruding portion of the prefabricated meniscus substitute extends into the positioning recess, and the bone screw is assembled to complete implantation of the meniscus substitute.

The application also provides a knee joint prosthesis. The knee joint prosthesis (not shown in the figures) according to the embodiment includes a meniscus substitute, and the meniscus substitute is a meniscus substitute including all or part of the abovementioned technical features.

From the above description, it can be seen that the abovementioned embodiments of the disclosure have the following technical effects.

The bone screw is disposed in the tibia in the penetration manner and fixedly connected with the base body, and the polymer joint body is disposed on the base body and cooperates with the femur structure. Due to the bone screw and the base body, the meniscus substitute may be effectively fixed on the tibia and prevented from being dislocated and deformed beyond an expectation on the tibia. When the femur structure moves relative to the tibia, the surface, facing the femur structure, of the polymer joint body is close to a primary meniscus and may be deformed along with rotation of the femur structure, so that an attachment area with the femur is ensured, and influence of local overuse damage of the polymer joint body on an overall using effect and service life of the meniscus substitute is avoided.

The above is only the preferred embodiment of the disclosure and not intended to limit the disclosure. For those skilled in the art, the disclosure may have various modifications and variations. Any modifications, equivalent replacements, improvements and the like made within the spirit and principle of the disclosure shall fall within the scope of protection of the disclosure.

What is claimed is:

1. A meniscus substitute sized and configured to be placed between a femur and a tibia of a patient, the meniscus substitute comprising:
   a base body sized and configured to be disposed on a tibial plateau of a tibia;
   a polymer joint body having a lower surface disposed on the base body and an upper articulating surface sized and configured to engage a femoral condyle; and
   a bone screw sized and configured to be screwed in the tibia and connected with the base body;
   wherein the base body comprises an integration layer, an isolation layer and a fusion layer, wherein the fusion layer is able to form contact fusion of the base body with the polymer joint body, the integration layer is sized and configured to allow bone tissue and soft tissues to grow into the integration layer, and the isolation layer is a metal or ceramic layer disposed between the fusion layer and the integration layer to prevent permeation of polymeric material from the integration layer into the fusion layer and to prevent permeation of polymeric material from the fusion layer into the integration layer, wherein the isolation layer comprises a bottom wall and a sidewall which are disposed at an angle of about 90 degrees, the bottom wall sized and configured to engage the tibial plateau of the tibia, the sidewall sized and configured to engage soft tissues around the meniscus substitute, the integration layer comprises a bone tissue integration portion disposed on the bottom wall and a soft tissue integration portion disposed on the sidewall, the bone tissue integration portion sized and configured to allow bone tissue ingrowth and the soft tissue integration portion sized and configured to allow soft tissue ingrowth, wherein the base body further comprises a soft tissue fixing portion, the soft tissue fixing portion is disposed on the sidewall of the isolation layer and extends out of the soft tissue integration portion, the soft tissue fixing portion comprises a suture slot and a suture column disposed in the suture slot, and the suture slot and the suture column form a passage that a suture line passes through to bundle and fix the soft tissues on the suture column, and wherein the meniscus substitute is C-shaped.

2. The meniscus substitute as claimed in claim 1, wherein the integration layer and the fusion layer are porous structures.

3. The meniscus substitute as claimed in claim 2, wherein a pore diameter of the porous structure of the bone tissue integration portion is 150 μm to 1,200 μm, and a pore diameter of the porous structure of the soft tissue integration portion is 400 μm to 2,000 μm.

4. The meniscus substitute as claimed in claim 1, wherein the integration layer and/or the fusion layer are/is made by use of a Three-Dimensional (3D) printing technology.

5. The meniscus substitute as claimed in claim 1, wherein the integration layer and/or the fusion layer are/is made by use of a metallic particle sintering technology.

6. The meniscus substitute as claimed in claim 1, wherein a positioning protruding portion is disposed on a side, facing the tibia, of the base body, a first threaded hole cooperated to the bone screw is formed in the positioning protruding portion.

7. The meniscus substitute as claimed in claim 6, wherein at least two sections of threads are disposed on the bone screw, a first thread and a second thread are disposed at two ends of the bone screw respectively, the first thread is disposed to be cooperated to the first threaded hole of the positioning protruding portion, the second thread is disposed to be cooperated to a second threaded hole formed in the tibia, and a nominal diameter of the second thread is not smaller than a nominal diameter of the first thread.

* * * * *